United States Patent
Noe et al.

(10) Patent No.: US 7,569,598 B2
(45) Date of Patent: *Aug. 4, 2009

(54) PROCESS FOR THE PREPARATION OF THE R,R (OR S,S) CONFIGURED GLYCOPYRRONIUM STEREOISOMER

(75) Inventors: Christian Noe, Vienna (AT); Martin Walter, Kriftel (DE)

(73) Assignee: Meda Pharma GmbH & Co. KG, Bad Homburg (DE)

( * ) Notice: Subject to any disclaimer, the term of this patent is extended or adjusted under 35 U.S.C. 154(b) by 441 days.

This patent is subject to a terminal disclaimer.

(21) Appl. No.: 10/540,187

(22) PCT Filed: Dec. 18, 2003

(86) PCT No.: PCT/EP03/14432

§ 371 (c)(1),
(2), (4) Date: Feb. 13, 2006

(87) PCT Pub. No.: WO2004/054971

PCT Pub. Date: Jul. 1, 2004

(65) Prior Publication Data

US 2006/0167275 A1    Jul. 27, 2006

(30) Foreign Application Priority Data

Dec. 18, 2002  (AT) .............................. A 1896/2002

(51) Int. Cl.
  *C07D 207/12*  (2006.01)
  *C07D 207/14*  (2006.01)
  *A61K 31/40*   (2006.01)
  *A61K 31/4025* (2006.01)
(52) U.S. Cl. ................ 514/424; 548/527; 548/551
(58) Field of Classification Search ................ 548/527, 548/551; 514/424
  See application file for complete search history.

(56) References Cited

U.S. PATENT DOCUMENTS 6,307,060 B1 * 10/2001  Noe et al. .................... 548/551

FOREIGN PATENT DOCUMENTS

WO          98/21183        5/1998

* cited by examiner

*Primary Examiner*—Golam M. M. Shameem
*Assistant Examiner*—Susannah Chung
(74) *Attorney, Agent, or Firm*—Laurence A. Greenberg; Werner H. Stemer; Ralph E. Locher

(57) ABSTRACT

The present invention relates to a process for the enrichment of the R,R- or S,S-configured glycopyrronium isomers and their thienyl derivatives having the R,S or S,R configuration.

16 Claims, No Drawings

PROCESS FOR THE PREPARATION OF THE R,R (OR S,S) CONFIGURED GLYCOPYRRONIUM STEREOISOMER

BACKGROUND OF THE INVENTION

FIELD OF THE INVENTION

The present invention relates to a process for the enrichment of the R,R- or S,S-configured glycopyrronium isomers and their thienyl analogs having R,S or S,R configuration.

Substances blocking muscarine receptors (anti-muscarinics) are employed worldwide to a great extent in numerous syndromes (Goodman & Gilman's *The Pharmacological Basis of Therapeutics*, Ninth Edition, McGraw-Hill, 1996; Mutschler, *Arzneimittelwirkungen* [Pharmaceutical Actions], 8th edition, Wissenschaftliche Verlagsgesellschaft Stuttgart, 2001), such as, for example, for the treatment of chronic obstructive airways diseases, disorders of voiding the bladder, kidney stone and gallstone colic, and irritation of the smooth musculature of the gastrointestinal canal (inter alia in irritable colon).

These actions are mediated by five different muscarine receptor subtypes. Individual ligand stereoisomers can have different affinities for these five receptor subtypes and thus preferably give rise to various—desired—actions as opposed to other—undesired—actions. Selective substances are to be preferred to nonselective active compounds because of their lower side effects, which in some cases can be achieved by the use of individual pure stereoisomers.

The glycopyrronium isomer having the R,R configuration has particularly favorable pharmacological properties (WO9821183). Its preparation is described (WO9821183). Glycopyrronium bromide and compounds derived therefrom comprise two stereogenic centers, from which the existence of in each case four stereoisomers results.

SUMMARY OF THE INVENTION

The present invention relates to a process for the preparation of 3R,2'R-configured glycopyrronium salts or of compounds related to glycopyrronium bromide having a corresponding spatial arrangement (e.g. in the case of thienyl on account of the Cahn-Ingold-Prelog rule=3R,2'S arrangement), characterized in that the desired stereoisomer is isolated from the enantio-merically pure diastereomer mixture of 3R,2'R isomer and 3R,2'S isomer or of 3R,2'R isomer and 3S,2'R isomer (or in the case of the thienyl analog from the enantiomerically pure diastereomer mixture of 3R,2'S isomer and 3R,2'R isomer or of 3R,2'S isomer and 3S,2'S isomer) by means of use of a suitable solvent during the quaternization and/or by means of recrystallization of the quaternary salts.

The process is in principle suitable in the same manner for preparing the antipodes (3S,2'S in the case of the phenyl compound, or 3S,2'R in the case of the thienyl analog) when the antipodes are employed (3S,2'S+3S,2'R or 3S,2'S+3R,2'S in the case of the phenyl compound, or 3S,2'R+3S,2'S or 3S,2'R+3R,2'R in case of the thienyl analog).

The present invention accordingly relates to a process a) for the isolation of the 3R,2'R stereoisomer of glycopyrronium bromide or iodide (formula II: A=Br or I),

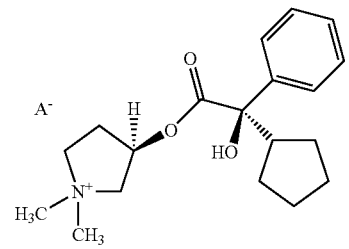

from the diastereomer mixture consisting essentially of the 3R,2'R isomer and 3R,2'S isomer (formula III)

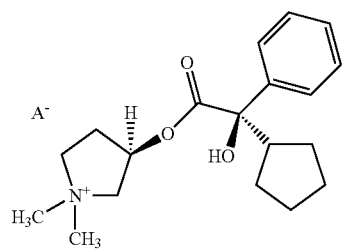

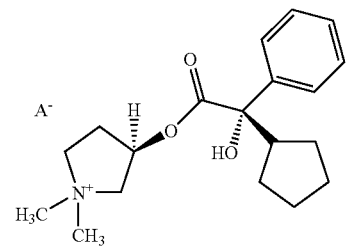

or from the diastereomer mixture consisting essentially of the 3R,2'R isomer and 3S,2'R isomer (formula IIIb)

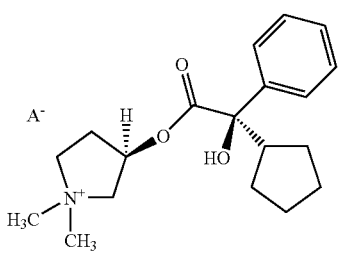

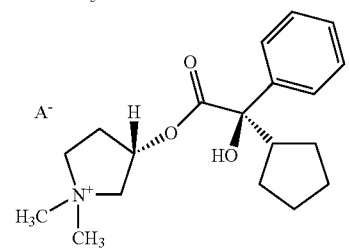

or b) for the isolation of the 3S,2'S isomer (formula IV: A=Br or I),

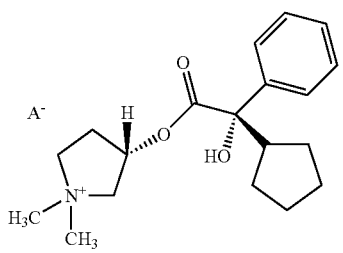

IV from the diastereomer mixture consisting essentially of the 3S,2'R isomer and 3S,2'S isomer (formula V)

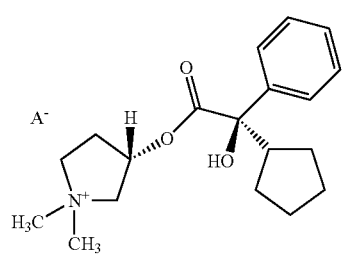

V

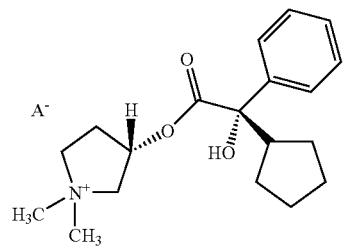

or from the diastereomer mixture consisting essentially of the 3R,2'S isomer and 3S,2'S isomer (formula Vb)

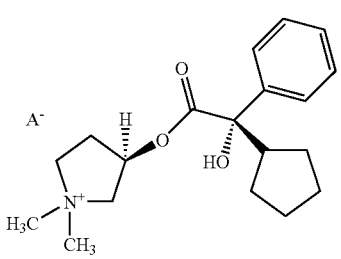

Vb

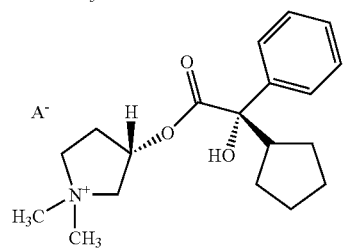

or c) for the isolation of the 3R,2'S stereoisomer of the thienyl analog of glycopyrronium (formula VI: A=Br or I),

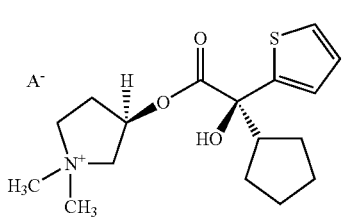

VI from the diastereomer mixture consisting essentially of the 3R,2'S isomer and 3R,2'R isomer (formula VII)

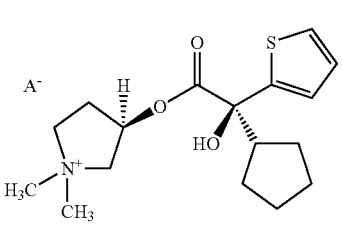

VII

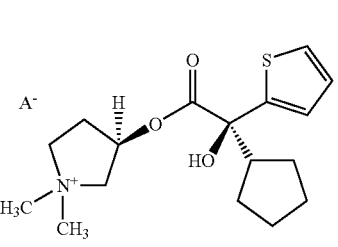

or from the diastereomer mixture consisting essentially of the 3R,2'S isomer and 3S,2'S isomer (formula VIIb)

VIIb or d) for the isolation of the 3S,2'R isomer (formula VIII: A=Br or I),

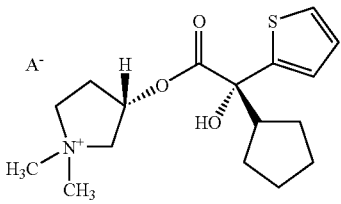

from the diastereomer mixture consisting essentially of the 3S,2'S isomer and 3S,2'R isomer (formula IX)

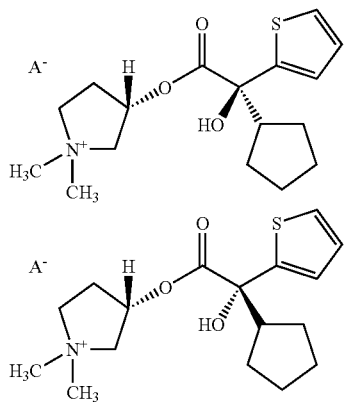

or from the diastereomer mixture consisting essentially of the 3S,2'R isomer and 3R,2'R isomer (formula IXb)

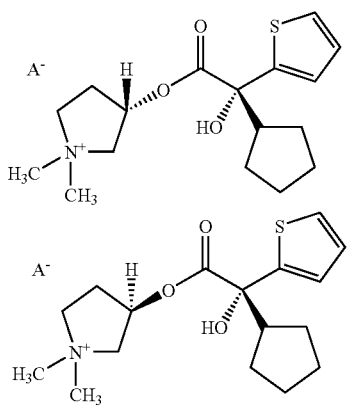

which is characterized in that in the quaternization to give the abovementioned diastereomer mixtures a suitable solvent is used in order to obtain the stereoisomer to be isolated in each case in enriched form as a precipitate and/or in that the diastereomer mixtures of the quaternary compounds described above are recrystallized in a suitable solvent or solvent mixture and in this process the isomer desired in each case is obtained in enriched form.

In one of the embodiments of the invention, solvents or solvent mixtures having a water content are used in the process, which leads to only the desired diastereomer being obtained in crystalline form, while the other diastereomer remains in solution or is obtained as an oil.

If the quaternizations of the diastereomer mixtures of the underlying tertiary bases to give said diastereomer mixtures of the ammonium salts are carried out in a suitable solvent having a sufficient water content, the desired stereoisomers are obtained in the precipitate in enriched form, while the other diastereomer in each case remains in solution.

For the reaction of the process according to the invention, a solvent in which the tertiary base and the resulting quaternary salts dissolve can be used for the quaternization and the addition of a further solvent brings about the crystallization of the desired isomer.

According to a further feature of the process according to the invention, a solvent is used for the quaternization in which both diastereomers of the resulting quaternary salts are poorly soluble and the addition of a further solvent leads to the undesired isomer going into solution or being obtained as an oil.

Suitable solvents for the quaternization which can be mentioned are, for example, branched and unbranched alcohols having a low molecular weight, such as methanol, ethanol, isopropanol, 1-propanol, tert-butanol, isobutanol, n-butanol, and also acetone, butanone or acetonitrile and the like, in each case pure or as mixtures with other solvents.

In practice, the solvent preferably used in the process according to the invention for the quaternization is acetone, preferably having a water content of approximately 0.5-2% (at a concentration of approximately 5-20% of base in solvent), even more preferably having a water content of approximately 1%.

According to a further feature of the process according to the invention, a solvent in which the diastereomer mixture dissolves readily is used for the recrystallization and a second solvent causing crystallization is added in order to bring about crystallization.

Preferably, methanol and/or ethanol are/is used for dissolving and crystallization is brought about using ethyl acetate and/or tert-butyl methyl ether.

According to a further feature, in the process according to the invention for recrystallization, the diastereomer mixture is dissolved in a heated solvent and crystallization is achieved by cooling.

Preferably, in the process according to the invention for recrystallization, the diastereomer mixture is dissolved at boiling heat in 2-propanol or ethanol and the crystallization is achieved on cooling to room temperature or below.

Preferably, in the process according to the invention for recrystallization, the diastereomer mixture was dissolved at boiling heat in 2-propanol which has a water content of approximately 0.2-3% (at a concentration of approximately 5-30% of quaternary ammonium salt in solvent), even more preferably approximately 0.5%, and the crystallization is achieved by cooling.

Suitable solvents for recrystallization which can be mentioned are, for example, branched and unbranched alcohols having a low molecular weight, such as methanol, ethanol, isopropanol, 1-propanol, tert-butanol, isobutanol, n-butanol, and also acetone, butanone or acetonitrile and the like, in each case pure or as mixtures with other solvents.

According to a further feature of the present invention, the process according to the invention is preferably used for the enrichment of the 3R,2'R isomer of glycopyrronium bromide.

Both in the quaternization of the underlying tertiary bases to give said diastereomer mixtures of the ammonium salts and in the recrystallization of the quaternary salts, by rewashing the precipitates of the desired stereoisomer, undesired isomer adhering to its surface is removed. This rewashing can also be carried out after isolation of the crude product by digesting the crude product in a solvent in which it only partially dissolves (preferably acetone having a water content of 1%), and subsequently filtering off the precipitate purified of the undesired diastereomer with suction.

The process according to the invention can also be advantageously utilized in combination with other processes for increasing the stereoisomer purity:

Should, for example, the bases employed for the quaternization or the quaternary ammonium salts already be present in diastereomer-enriched form, this enrichment can be optimized using the process according to the invention.

On the other hand, the process according to the invention in the sense of a prepurification can already cause a high stereoisomer excess, which is advantageous when using a subsequent process for further increasing the stereoisomer purity.

The claimed process is suitable, starting from the 3R,2'R/3R,2'S diastereomer mixture of the tertiary glycopyrrolate resulting when using the 3R-configured enantiomerically pure aminoalcohol and the racemic acid (or a corresponding ester or an activated acid derivative) or, when using 3S-configured aminoalcohol, the resulting mixture of 3S,2'R and 3S,2'S isomers, by means of use of a suitable solvent during the quaternization and/or by recrystallization of the quaternary ammonium salts for enriching the isomer in which the asymmetric centers of the aminoalcohol component and the acid component bear the same indication of the absolute configuration (that is 3R,2'R and 3S,2'S; formula Ia). By repeating the crystallization procedure, the stereoisomer purities can be further perfected.

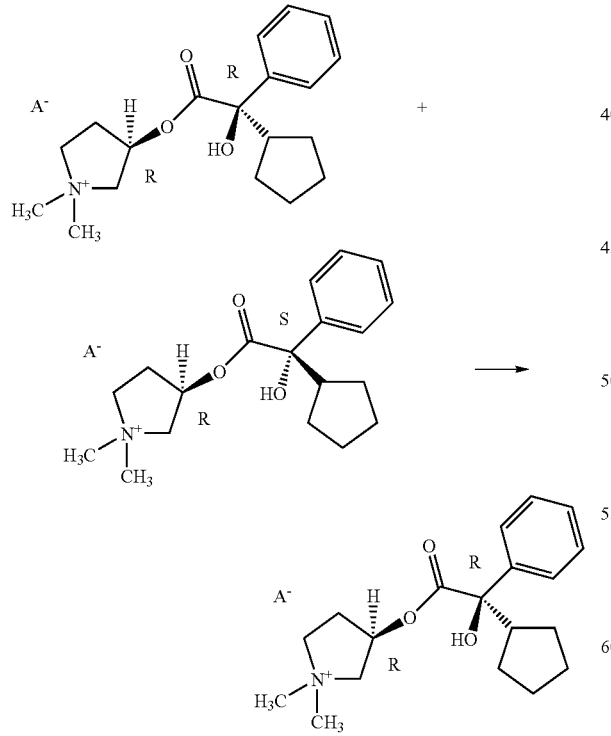

Formula Ia
or

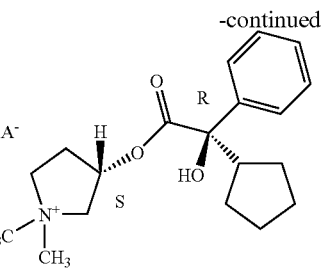

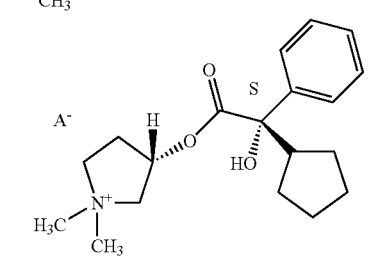

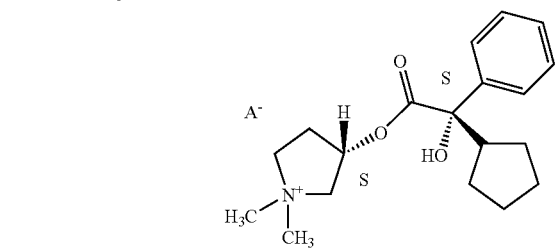

In the case of the 2-thienyl analog, starting from the diastereomer mixture of 3R,2'S isomer and 3R,2'R isomer or from the 3S,2'R/3S,2'S diastereomer mixture, on account of the higher priority of the thienyl radical the stereoisomers which bear the opposite indication of the configuration (that is 3R,2'S and 3S,2'R; formula Ib), but have the same spatial arrangement as in the phenyl compound, are obtained.

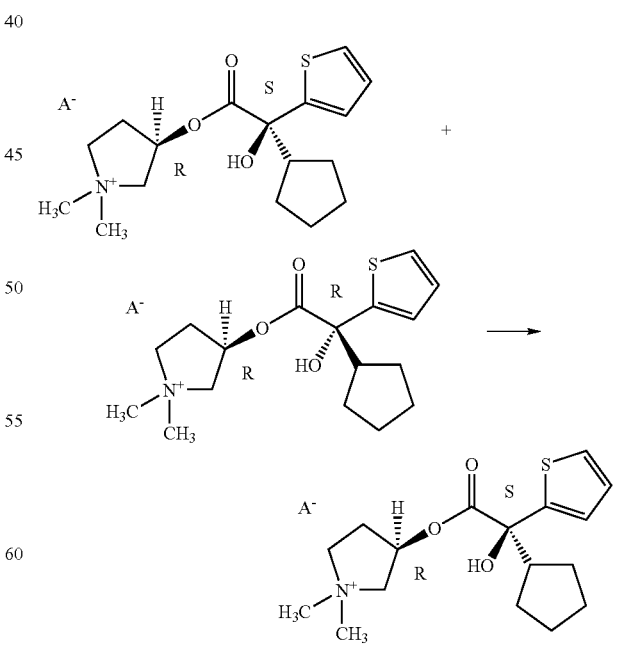

Formula Ib
or

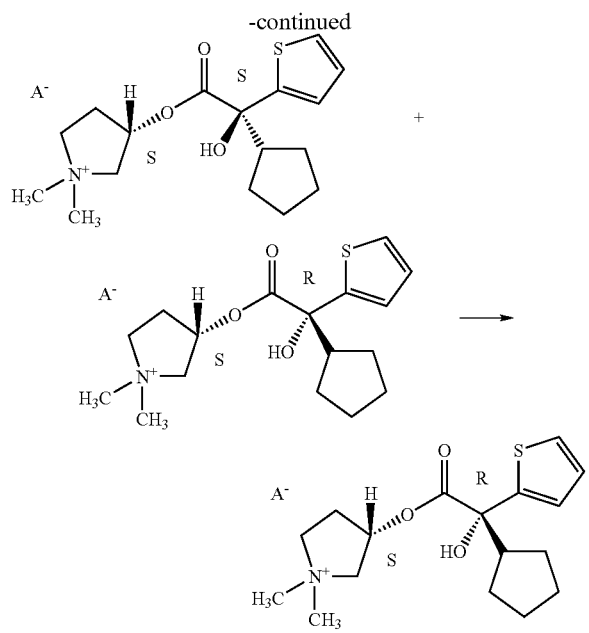

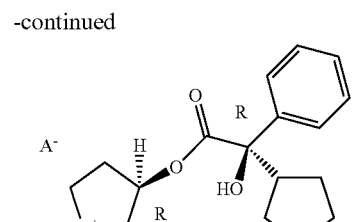

Formula Ic or

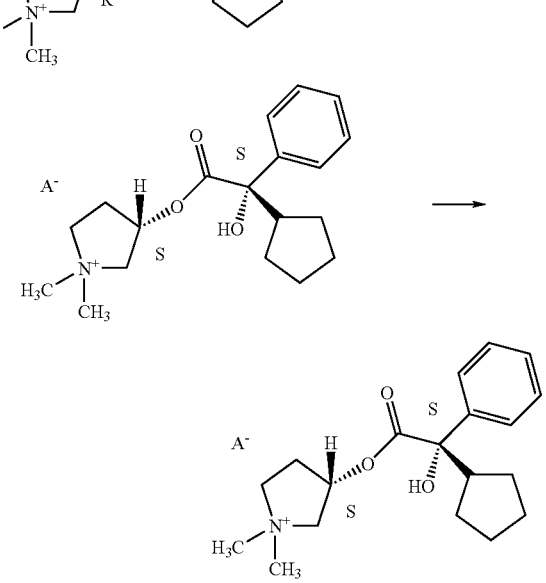

Alternatively to this, it is also possible to start from an enantiomerically pure acid component (or a corresponding ester or an activated acid derivative) and a racemic aminoalcohol and to isolate the desired stereoisomer from the resulting basic diastereomer mixture by means of use of a suitable solvent during the quaternization and/or by means of recrystallization of the quaternary salts.

In the case of the 2R-configured acid component, starting from the resulting 3R,2'R/3S,2'R diastereomer mixture of the tertiary glycopyrrolate or in the case of the use of 2S-configured acid component, starting from the resulting mixture of 3R,2'S and 3S,2'S isomers, by means of use of a suitable solvent during the quaternization and/or by recrystallization of the quaternary ammonium salts, the isomer is obtained here in which the asymmetric centers of the aminoalcohol component and of the acid component carry the same indication of the absolute configuration (that is 3R,2'R or 3S,2'S; formula Ic).

In the case of the 2-thienyl analog, starting from the diastereomer mixture of 3R, 2'S isomer and 3S,2'S isomer or from the 3R,2'R/3S,2'R diastereomer mixture, on account of the higher priority of the thienyl radical the stereoisomers which bear the opposite indication of the configuration (that is 3R,2'S and 3S,2'R; formula Id), but have the same spatial arrangement as in the case of the phenyl compound, are obtained.

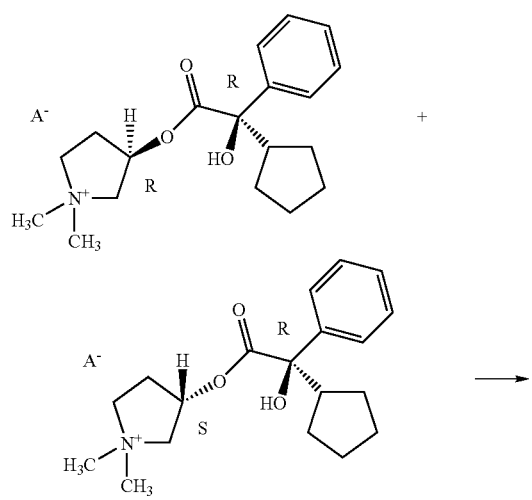

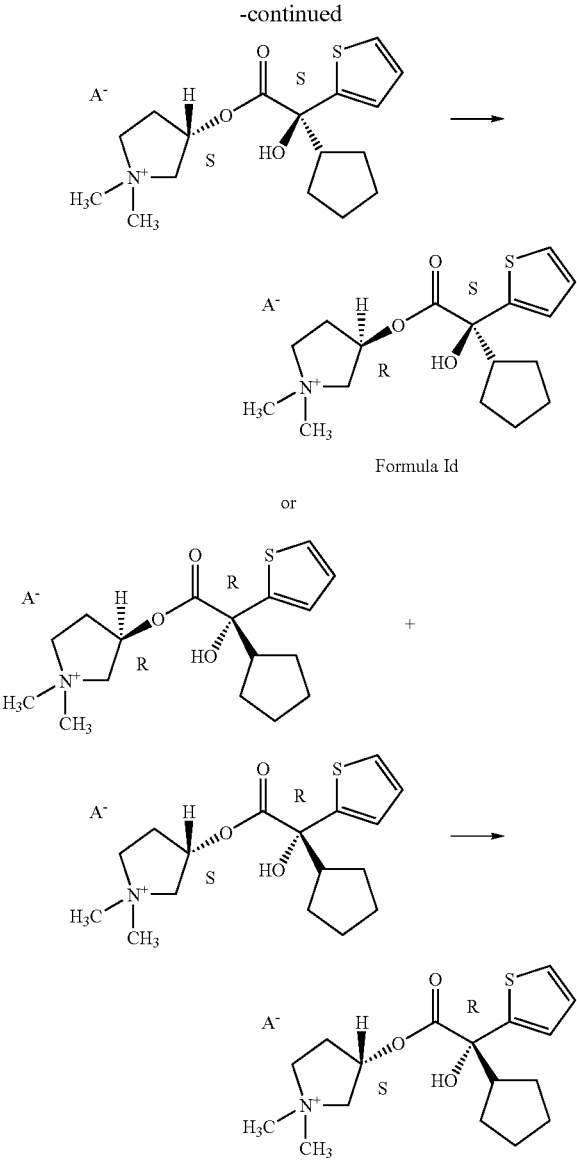

In the case of glycopyrronium bromide, however, if a mixture of all four isomers of the quaternary ammonium salt is crystallized, the solid obtained is a mixture of 3R,2'S isomer and 3S,2'R isomer, i.e. the isomer having the most advantageous pharmacological properties is lost in this method.

For the isolation of said stereoisomers from the diastereomer mixtures of quaternary ammonium salts, the use of various crystallization methods is possible.

Suitable solvents for the recrystallization are generally all solvents and solvent mixtures in which the diastereomer mixture is brought into solution—optionally by heating—and crystallization can be brought about by suitable measures, the desired isomer being obtained in enriched form in the solid.

Suitable measures which may be mentioned in order to initiate crystallization in the solution of the diastereomer mixture are: cooling of the solution, addition of further solvents in which the desired isomer has a lower solubility than in the original solvent, concentration of the solvent volume or removal of one component of the solvent mixture in which the desired isomer has a higher solubility than in the remaining solvent mixture.

As has been discovered, the undesired isomer shows strongly hygroscopic behavior, while this is not to be observed in the case of the desired isomer. In one of the embodiments of the process claimed, in which a solvent having sufficient water content is used or water is added to an anhydrous solvent, this characteristic leads to the desired diastereomer exclusively being obtained in crystalline form, while the other diastereomer remains in solution or forms an oil which can be separated off.

The use of volatile solvents which are easy to remove from the solid obtained is preferred.

Solvents from which exclusively the desired stereoisomer crystallizes as a solid are particularly preferred.

The process claimed here allows the desired stereoisomer to be obtained inexpensively in very high purity with a low technical outlay.

The consumption of starting materials on account of the isomer separation after the last reaction step is relatively high compared with other conceivable processes in which the separation of isomers takes place in an earlier section of the synthesis route.

This putative disadvantage, however, is over-compensated for by the simplicity with which the process claimed can be carried out.

In particular, the fact that in this process the desired isomer has a drastically increased tendency to crystallize compared with the undesired diastereomer constitutes the particular advantage of this process and earns special consideration.

The enantiomerically pure aminoalcohol component can be prepared according to techniques which are described in the literature (Razematspaltung und asymmetrische Synthese [Resolution of racemates and asymmetric synthesis]: *J. Med. Chem.* 34 (1991) 1314-1328). The same also applies to the acid component: (Razematspaltung [Resolution of racemates]: *Bioorg. Med. Chem.* 7 (1999) 2555-2567; asymmetric synthesis: *Bioorg. Med. Chem. Lett.* 9 (1999) 2037-2038). The feasibility of the process is thus provided.

With respect to the industrial utility, the method according to the invention shows marked advantages compared with other conceivable processes for the preparation of said stereoisomer from the respective diastereomer mixture. Thus, in the process according to the invention no additional chiral auxiliaries, which in some cases are very expensive and possibly not accessible at all in larger amounts, are necessary. The use of a single enantiomerically pure substance, which is, in any case, a structural unit of the product, suffices. Thus the preparation of the pure isomer is hardly more expensive than the production of the mixture of all four isomers, or even of the isomer mixture of 3R,2'S- and 3S,2'R-glycopyrronium bromide presently on the market. In the last-mentioned case, the therapeutically most useful isomer is not even contained in the product.

Moreover, the process according to the invention avoids additional working steps which are necessary in resolutions of racemates, such as crystallization using chiral bases or acids, repeated recrystallization of the resulting salts, liberation from said salts and in the case of the acid component prior hydrolysis of the ester and fresh methyl ester The following examples serve for the description of the invention and are not a restriction thereof.

EXAMPLE 1

Preparation of (3R,2'R)-[(2-cyclopentyl-2-hydroxy-2-phenylacetyl)oxy]-1,1-dimethylpyrrolidinium bromide (Formula Ia: $A^-=Br^-$)

Transesterification 0.17 mol of (3R)-1-methyl-3-pyrrolidinol and 0.17 mol of racemic methyl 2-cyclopentyl-2-hydroxy-2-phenyl-acetate are introduced into 800 ml of n-heptane abs. in a dry reaction apparatus. Subsequently, 400 ml of heptane are removed by distillation to remove all traces of moisture and drawn off through the water separator. After cooling, 0.9 g of NaOMe (10 mol %) is added and in turn heated to boiling. The amount of solvent passing over is replaced continuously by means of a dropping funnel for 5-6 h. After aqueous work up of the reaction mixture and extraction with ether, the organic phase is dried over $Na_2SO_4/K_2CO_3$ 2:1. Removal of drying agent and solvent yields the free base in 82% yield.

Quaternization:

The free base is quaternized by addition of 3 eq of methyl bromide, dissolved in tert-butyl methyl ether, and the product obtained in crystalline form is filtered off with suction in 93% yield. The resulting diastereomer mixture of (3R,2'S)- and (3R,2'R)-[(2-cyclopentyl-2-hydroxy-2-phenylacetyl)oxy]-1,1-dimethyl-pyrrolidinium bromide is present in a ratio of approximately one to one.

Separation of Diastereomers by Recrystallization:

The crude product is dissolved in 250 ml of methanol, diluted with 300 ml of ethyl acetate and treated with 450 ml of diethyl ether. After two days, the resulting crystals are filtered off with suction and recrystallized a second time. The (3R,2'R) isomer is obtained in 50% yield.

Analytical Data:

Appearance: Colorless Crystals $^1$H-NMR ($D_2O$) (300 MHz): δ=7.55-7.52 (m, 2H, phenyl); 7.37-7.24 (m, 3H, phenyl); 5.42-5.34 (m, 1H); 4.67 (s, $H_2O$); 3.65 (dd, 1H); 3.61-3.43 (m, 2H); 3.40 (dd, 1H); 3.13-2.98 (m, 1H, cyclopentylmethine); 3.04 (s, 3H, $NCH_3$, (3R,2'R)); 2.75 (s, 3H, $NCH_3$, (3R,2'R)); 2.71-2.55 (m, 1H); 2.30-2.17 (m, 1H (3R,2'R)); 1.65-1.43 (m, 7H, cyclopentyl); 1.19-1.05 (m, 1H)

The diastereomeric compounds for this differ essentially by the shifts of the following signals: 3.08 (s, $NCH_3$); 2.91 (s, $NCH_3$); 2.11-1.92 (m)

From the comparison of the integrals of the signals at 2.75 (s, 3H, $NCH_3$, (3R,2'R)) and 2.91 (s, $NCH_3$ (diastereomers)), a diastereomer excess of over 98% de results for the R,R-glycopyrronium bromide. The enantiomeric purity results from the use of enantiomerically pure 3R-N-methylpyrrolidinol.

$^{13}$C-NMR ($D_2O$) (50 MHz): δ=177.1 (s, 1'-COO); 143.2 (s, phenyl); 131.4 (d, phenyl); 131.0 (d, phenyl); 128.8 (d, phenyl); 83.2 (s); 76.6 (d); 72.9 (t); 67.6 (t); 56.3 (q, $NCH_3$); 55.6 (q, $NCH_3$); 47.5 (d, cyclopentyl-methine); 32.4 (t); 29.2/28.8/28.7/28.4 (t, cyclo-pentylmethylene)

Empirical formula/mass of the cation: $(C_{19}H_{28}NO_3)^+$ $(Br)^-$/318.44; (ESI+) mass spectrum: 318.2=$M^+$ Elemental analysis: calc.: C 57.29 H 7.09 N 3.52; fnd: C 57.41 H 7.00 N 3.54

The determination of the absolute configuration was carried out by means of X-ray structural analysis.

EXAMPLE 2

Preparation of (3R,2'R)-[(2-cyclopentyl-2-hydroxy-2-phenylacetyl)oxy]-1,1-dimethylpyrrolidinium bromide (Formula Ia: $A^*=Br^-$)

Transesterification and quaternization are carried out as described under example 1.

The separation of diastereomers is carried out by means of recrystallization of the diastereomer mixture in isopropanol. For this, the crude product is dissolved at boiling heat in the 8-fold amount by weight of isopropanol. The solution is allowed to stand overnight at room temperature and the resulting crystals are filtered off with suction. This procedure is repeated once again. The (3R,2'R)-glycopyrronium bromide thus obtained leads to the same analytical data as described under example 1.

EXAMPLE 3

Preparation of (3R,2'R)-[(2-cyclopentyl-2-hydroxy-2-phenylacetyl)oxy]-1,1-dimethylpyrrolidinium iodide (Formula Ia: $A^*=I^-$)

Transesterification, quaternization (with methyl iodide) and separation of diastereomers are carried out as described under example 1.

The (3R,2'R)-glycopyrronium iodide thus obtained leads to the same NMR spectroscopic data as described under example 1.

EXAMPLE 4

Preparation of (3R,2'S)-3-[(2'-cyclopentyl-2'-hydroxy-2'-(2''-thienyl)acetyl)oxy]-1,1-dimethylpyrrolidinium bromide (Formula Ib: $A^-=Br^-$)

Transesterification (with (3R)-1-methyl-3-pyrrolidinol and racemic methyl 2-cyclopentyl-2-hydroxy-2- (2'-thienyl) acetate), quaternization and separation of diastereomers are carried out as described under example 1.

$^1$H-NMR (300 MHz, $D_2O$): δ=7.33 (d, 1H, thienyl); 7.13 (d, 1H, thienyl); 6.96 (dd, 1H, thienyl); 5.50-5.42 (m, 1H); 4.67 (s, $H_2O$); 3.78-3.62 (m, 2H); 3.58-3.47 (m, 2H); 3.08 (s, 3H, $NCH_3$, (3R,2'S)); 3.01-2.83 (m, 4H, $NCH_3$, (3R,2'S) and cyclopentylmethine); 2.76-2.62 (m, 1H); 2.37-2.22 (m, 1H (3R,2'S)); 1.65-1.20 (m, 8H, cyclopentylmethylene).

The diastereomeric compounds for this (3R,2'R and 3S,2'S) differ essentially by the shifts of the following signals: 3.11 (s, $NCH_3$); 3.04 (s, $NCH_3$); 2.15-2.03 (m).

The diastereomer excess was determined by means of a capillary electrophoretic method at over 98% de. The enantiomeric purity results from the use of enantiomerically pure 3R-N-methylpyrrolidinol.

$^{13}$C-NMR (50 MHz, $D_2P$): δ=176.2 (s, 1'-COO); 147.7 (s, thienyl); 130.1 (d, thienyl); 128.8 (d, thienyl); 128.4 (d, thienyl); 82.2 (s); 76.9 (d); 72.9 (t); 67.7 (t); 56.4 (q, $NCH_3$); 55.8 (q, $NCH_3$); 49.4 (d, cyclopentyl-methine); 32.5 (t); 29.2/29.0/28.7/28.4 (t, cyclo-pentylmethylene).

Empirical formula/mass of the cation: $(C_{17}H_{28}NO_3S)^+$ $(Br)^-$/324.47 (ESI+) mass spectrum: 324.4=$M^+$ The determination of the absolute configuration was carried out by means of X-ray structural analysis.

EXAMPLE 5

Preparation of (3S,2'S)-[(2-cyclopentyl-2-hydroxy-2-phenylacetyl)oxy]-1,1-dimethylpyrrolidinium bromide (Formula Ia: $A^-=Br^-$)

Transesterification (with (3S)-1-methyl-3-pyrrolidinol and racemic methyl 2-cyclopentyl-2-hydroxy-2-phenyl-acetate), quaternization and separation of diastereomers are carried out as described under example 1.

The NMR spectroscopic data correspond to the values indicated in example 1 for the enantiomeric compound.

EXAMPLE 6

Preparation of (3S,2'R)-3-[(2'-cyclopentyl-2¹-hydroxy-2'-(2"-thienyl)acetyl)oxy]-1,1-dimethylpyrrolidinium bromide (Formula Ib: $A^-=Br^-$)

Transesterification (with (3S)-1-methyl-3-pyrrolidinol and racemic methyl 2-cyclopentyl-2-hydroxy-2-(2'-thienyl) acetate), quaternization and separation of diastereomers are carried out as described under example 1.

The NMR spectroscopic data correspond to the values indicated in example 4 for the enantiomeric compound.

EXAMPLE 7

Preparation of (3R,2'R)-[(2-cyclopentyl-2-hydroxy-2-phenylacetyl)oxy]-1,1-dimethylpyrrolidinium bromide (Formula Ia: $A^-=Br^-$)

Transesterification (with racemic 1-methyl-3-pyrrolidinol and methyl (2R)-2-cyclopentyl-2-hydroxy-2-phenylacetate) and quaternization are carried out as described under example 1.

The separation of diastereomers is carried out as described in example 2, by means of recrystallization of the diastereomer mixture in isopropanol.

The NMR spectroscopic data correspond to the values indicated under example 1.

EXAMPLE 8

Preparation of (3R,2'S)-3-[(2'-cyclopentyl-2'-hydroxy-2'-(2"-thienyl)acetyl)oxy]-1,1-dimethylpyrrolidinium bromide (Formula Ib: $A^-=Br^-$)

Transesterification (with racemic 1-methyl-3-pyrrolidinol and methyl (2S)-2-cyclopentyl-2-hydroxy-2-(2'-thienyl)acetate) and quaternization are carried out as described under example 1.

The separation of diastereomers is carried out as described in example 1, by means of recrystallization of the diastereomer mixture in a mixture of methanol, ethyl acetate and diethyl ether.

The NMR spectroscopic data correspond to the values indicated under example 4.

EXAMPLE 9

Preparation of (3S,2'S)-[(2-cyclopentyl-2-hydroxy-2-phenylacetyl)oxy]-1,1-dimethylpyrrolidinium bromide (Formula Ia: $A^*=Br^-$)

Transesterification (with racemic 1-methyl-3-pyrrolidinol and methyl (2S)-2-cyclopentyl-2-hydroxy-2-phenylacetate) and quaternization are carried out as described under example 1.

The separation of diastereomers is carried out as described in example 2, by means of recrystallization of the diastereomer mixture in isopropanol.

The NMR spectroscopic data correspond to the values indicated in example 1 for the enantiomeric compound.

EXAMPLE 10

Preparation of (3S,2'R)-3-[(2'-cyclopentyl-2'-hydroxy-2'-(2"-thienyl)acetyl)oxy]-1,1-dimethylpyrrolidinium bromide (Formula Ib: $A^-=Br^-$)

Transesterification (with racemic 1-methyl-3-pyrrolidinol and methyl (2R)-2-cyclopentyl-2-hydroxy-2-(2'-thienyl)acetate) and quaternization are carried out as described under example 1. The separation of diastereomers is carried out as described in example 1, by means of recrystallization of the diastereomer mixture in a mixture of methanol, ethyl acetate and diethyl ether.

The NMR spectroscopic data correspond to the values indicated in example 4 for the enantiomeric compound.

EXAMPLE 11

Preparation of (3R,2'R)-[(2-cyclopentyl-2-hydroxy-2-phenylacetyl)oxy]-1,1-dimethylpyrrolidinium bromide (Formula Ia: $A^-=Br^-$)

Transesterification and quaternization are carried out as described under example 1 with the difference that the methylation is carried out in isopropanol. Filtering off the resulting precipitate with suction yields a diastereomer ratio of 98% of 3R,2'R isomer and 2% of 3R,2'S isomer.

The further separation of diastereomers is carried out as described in example 2. Since already diastereomerically enriched crude product is used for the recrystallization, a higher stereoisomer purity is obtained with the same number of crystallization steps or a lower number of recrystallizations is needed for the same enrichment.

The (3R,2'R)-glycopyrronium bromide thus obtained leads to the same analytical data as described under example 1.

EXAMPLE 12

Preparation of (3R,2'R)-[(2-cyclopentyl-2-hydroxy-2-phenylacetyl)oxy]-1,1-dimethylpyrrolidinium bromide (Formula Ib: $A^-=Br^-$)

Transesterification and quaternization are carried out as described under example 1 with the difference that the methylation is carried out in acetone. Filtering off the resulting precipitate with suction yields a diastereomer ratio of 90% of 3R,2'R isomer and 10% of 3R,2'S isomer.

The further separation of diastereomers is carried out as described in example 11.

The (3R,2'R)-glycopyrronium bromide thus obtained leads to the same analytical data as described under example 1.

EXAMPLE 13

Preparation of (3R,2'R)-[(2-cyclopentyl-2-hydroxy-2-phenylacetyl)oxy]-1,1-dimethylpyrrolidinium bromide.

The transesterification is carried out as described under example 1.

Quaternization:

The free base, dissolved in acetone which has a water content of 1%, is quaternized by addition of 1.3 eq of methyl bromide and the product obtained in crystalline form is filtered off with suction in approximately 74% yield (based on the desired diastereomer). The diastereomer ratio is 95 to 5 or better.

The further separation of diastereomers is carried out as described in example 2. Since already diastereomerically enriched crude product is used for the recrystallization, a higher stereoisomer purity is obtained with the same number of crystallization steps or a lower number of recrystallizations is needed for the same enrichment.

The (3R,2'R)-glycopyrronium bromide thus obtained leads to the same analytical data as described under example 1.

In otherwise the same procedure, but using acetone with a water content of between 0.5 and 2%, in which sufficient base is dissolved that it is present with respect to the amount of solvent with a concentration of between 5 and 20 percent by weight, comparable results are obtained in the quaternization with respect to the enrichment of diastereomers.

EXAMPLE 14

Preparation of (3R,2'R)-[(2-cyclopentyl-2-hydroxy-2-phenylacetyl)oxy]-1,1-dimethylpyrrolidinium bromide.

The transesterification is carried out as described under example 1, the quaternization as described in example 13.

The separation of diastereomers is carried out by means of recrystallization of the diastereomer mixture in isopropanol which has a water content of 0.5%. After repetition of the recrystallization only once, the proportion of undesired diastereomer is less than 0.5%.

The (3R,2'R)-glycopyrronium bromide thus obtained leads to the same analytical data as described under example 1.

In otherwise the same procedure, but using isopropanol with a water content of between 0.2% and 3%, of which sufficient is added that the crude product is present with respect to the amount of solvent with a concentration of between 5 and 30 percent by weight, comparable results are obtained with respect to the enrichment of diastereomers after recrystallization twice.

EXAMPLE 15

Preparation of (3R,2'R)-[(2-cyclopentyl-2-hydroxy-2-phenylacetyl)oxy]-1,1-dimethylpyrrolidinium bromide.

The transesterification is carried out in a similar manner to that described under example 1.

Quaternization:

6 kg of the glycopyrrolate base are dissolved in 55 liters of acetone which has a water content of approximately 1%, and the mixture is cooled to −5° C. (±5). 1.3 equivalents of gaseous bromomethane are slowly passed in such that it can condense into the cooled solution. Subsequently, the mixture is warmed to room temperature for 3 hours and stirred for a further 3 hours. The resulting precipitate is filtered off and rewashed with 10 liters of acetone to remove methyl bromide from the product.

By drying, the crude product is obtained as a crystalline, white precipitate in approximately 70% yield (based on the desired diastereomer), in which less than 5% of the undesired diastereomer is contained.

Recrystallization:

20 liters of isopropanol which has a water content of 0.5% of water are added to the precipitate and this mixture is heated under reflux. When the solid has completely dissolved, the solution is filtered in order to purify it of suspended substances. For crystallization, the solution is cooled to room temperature over a period of 3 hours. After a further 3 hours, the deposited product can be filtered off with suction, rewashing with 5 liters of isopropanol.

A single repetition of the recrystallization process suffices in order to obtain (3R,2'R)-glycopyrronium bromide in a quality which exceeds the requirements of an active compound for the production of medicaments, i.e. in total less than 0.5% of the other three stereoisomers and less than 1% total impurities are contained.

EXAMPLE 16

Preparation of (3R,2'R)-[(2-cyclopentyl-2-hydroxy-2-phenylacetyl)oxy]-1,1-dimethylpyrrolidinium bromide (Formula Ia: $A^-=Br^-$)

Transesterification and quaternization are carried out as described under example 1.

The resulting diastereomer mixture of (3R,2'S)- and (3R,2'R)-[(2-cyclopentyl-2-hydroxy-2-phenylacetyl)oxy]-1,1-dimethylpyrrolidinium bromide is isolated in a ratio of approximately one to one.

3 g of this diastereomer mixture are suspended in 21 ml of acetone which has a water content of 1% and the mixture is stirred at room temperature for 6 hours. Filtering off the solid with suction yields 1.047 g, in which the desired diastereomer is contained in 93% de.

EXAMPLE 17

Preparation of (3R,2'R)-[(2-cyclopentyl-2-hydroxy-2-phenylacetyl)oxy]-1,1-dimethylpyrrolidinium bromide (Formula Ia: $A^-=Br^-$)

Transesterification and quaternization are carried out as described under example 1.

The resulting diastereomer mixture of (3R,2'S)- and (3R,2'R)-[(2-cyclopentyl-2-hydroxy-2-phenylacetyl)oxy]-1,1-dimethylpyrrolidinium bromide is isolated in a ratio of approximately one to one.

8 g of this diastereomer mixture are dissolved in 40 ml of boiling isopropanol which has a water content of 0.5% and the solution is subsequently cooled to room temperature over a period of 3 hours. After stirring at room temperature for a further 3 hours, the deposited product is filtered off with suction. 2.227 g of solid are obtained, in which the desired diastereomer is contained in 96% de.

We claim:
1. A process for the isolation
   a) of the 3R,2'R stereoisomer of glycopyrronium bromide or iodide (formula II: A=Br or I),

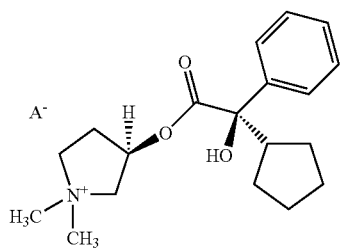

II or
   b) of the 3S,2'S stereoisomer (formula IV: A=Br or I),

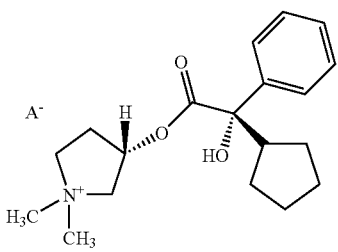

IV or
   c) of the 3R,2'S stereoisomer of the thienyl analog of glycopyrronium (formula VI: A=Br or I),

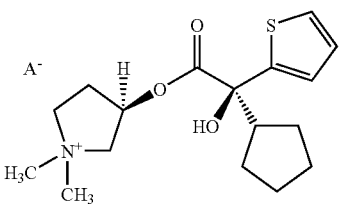

VI or
   d) of the 3S,2'R stereoisomer (formula VIII: A=Br or I),

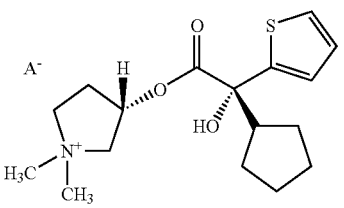

VIII where
   a) for the isolation of the 3R,2'R stereoisomer of glycopyrronium bromide or iodide (formula II: A=Br or I),

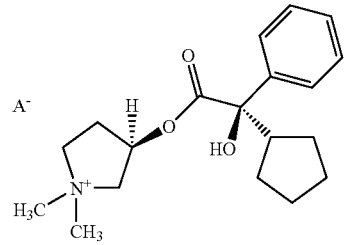

II the diastereomer mixture consisting essentially of the 3R,2'R isomer and 3R,2'S isomer (formula III)

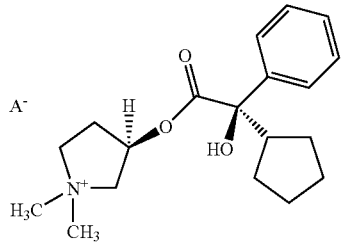

III

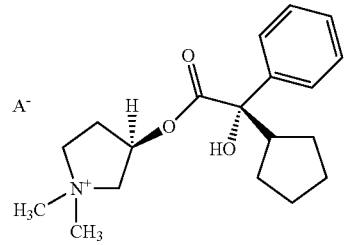

or the diastereomer mixture consisting essentially of the 3R,2'R isomer and 3S,2'R isomer (formula IIIb)

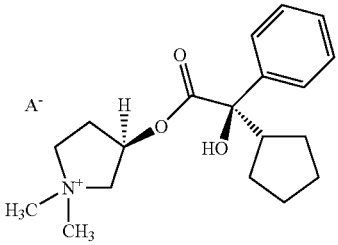

IIIb

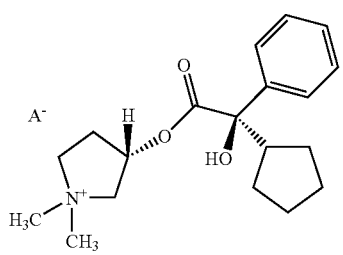

or b) for the isolation of the 3S,2'S isomer (formula IV: A=Br or I),

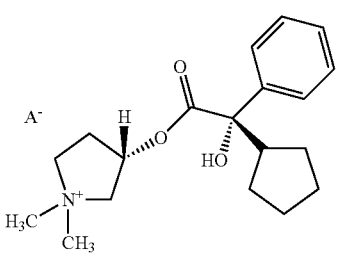

IV the diastereomer mixture consisting essentially of the 3S,2'R isomer and 3S,2'S isomer (formula V)

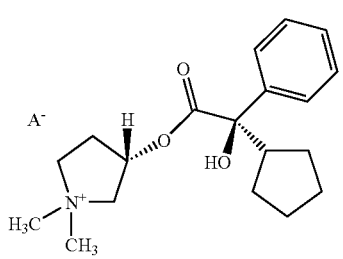

V

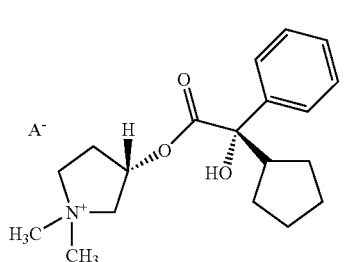

or the diastereomer mixture consisting essentially of the 3R,2'S isomer and 3S,2'S isomer (formula Vb)

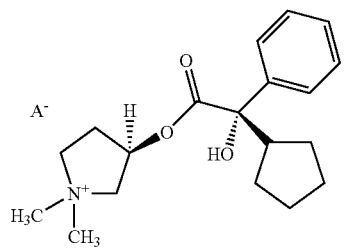

Vb

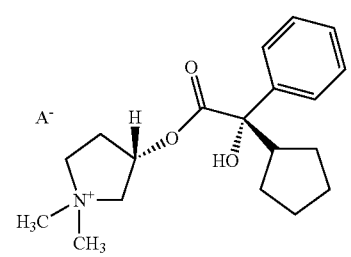

or c) for the isolation of the 3R,2'S stereoisomer of the thienyl analog of glycopyrronium (formula VI: A=Br or I),

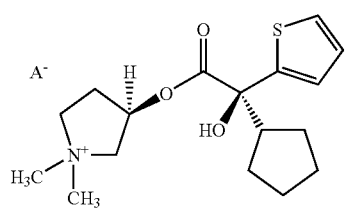

VI the diastereomer mixture consisting essentially of the 3R,2'S isomer and 3R,2'R isomer (formula VII)

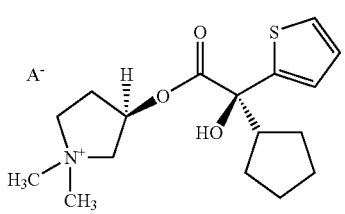

VII

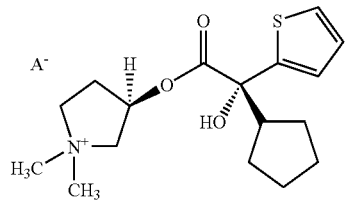

or the diastereomer mixture consisting essentially of the 3R,2'S isomer and 3S,2'S isomer (formula VIIb)

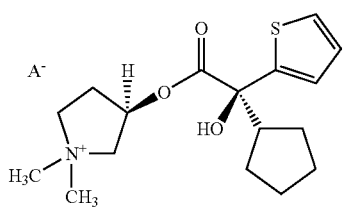

VIIb

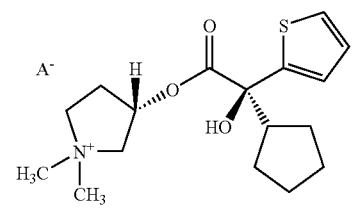

or d) for the isolation of the 3S,2'R isomer (formula VIII: A=Br or I),

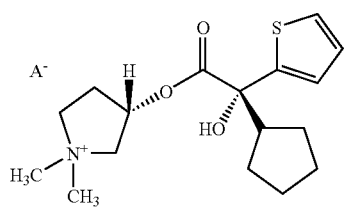

VIII the diastereomer mixture consisting essentially of the 3S,2'S isomer and 3S,2'R isomer (formula IX)

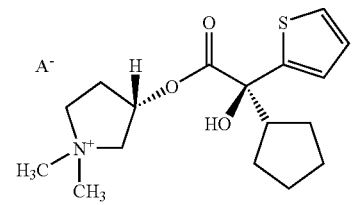

IX

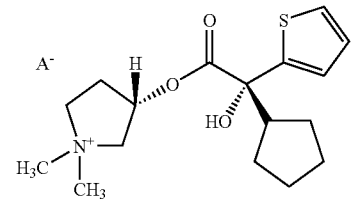

or the diastereomer mixture consisting essentially of the 3S,2'R isomer and 3R,2'R isomer (formula IXb)

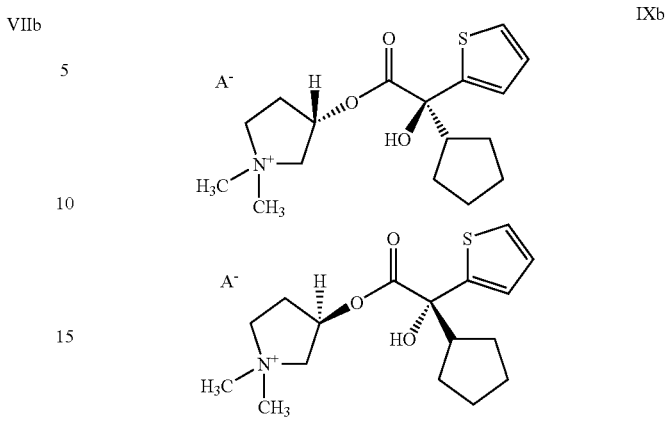

IXb is combined for re-crystallizing and the stereoisomer to be isolated in each case is precipitated and obtained in enriched form, wherein for the preparation of those tertiary, basic diastereomer mixtures employed in the quaternization which lead to the abovementioned quaternary diastereomer mixtures a solvent is selected from the group consisting of branched and unbranched alcohols having one to four carbon atoms, acetone, butanone and acetonitrile in which the diastereomer mixture dissolves readily in said solvent, and said solvent consisting of branched and unbranched alcohols having one to four carbon atoms is preferably methanol, ethanol, or combinations thereof, and the stereoisomer to be isolated in each case is precipitated to be obtained in enriched form, using a second solvent preferably selected from ethyl acetate and/or tert-butyl methyl ether causing crystallization.

2. The process as claimed in claim 1, in which solvent having a water content not exceeding approximately 5% is used which leads to only the desired diastereomer being obtained in crystalline form, while the other diastereomer remains in solution or is obtained as an oil.

3. The process as claimed in claim 1, in which the solvent used in the quaternization to give said diastereomer mixtures of the quaternary salts is isopropanol or acetone and thus said stereoisomers are isolated in enriched form in the resulting precipitate.

4. The process as claimed in claim 1, in which for the recrystallization the diastereomer mixture is dissolved in a heated solvent and crystallization takes place by cooling.

5. The process as claimed in claim 4, in which the heated solvent is 2-propanol or ethanol.

6. The process as claimed in claim 1 for the enrichment of the 3R,2'R isomer of glycopyrronium bromide.

7. The process as claimed in claim 1 as a prepurification stage for obtaining a primary enrichment of diastereomers or, if enrichment has already taken place, to give a further increase in the diastereomer purity.

8. The process as claimed in claim 1, a solvent having a water content of approximately 0.2-3%, being used in the recrystallization.

9. The process as claimed in claim 1, wherein the water content of the solvent is approximately 0.5-2%.

10. The process as claimed in claim 1, wherein the water content of the solvent is approximately 1%.

11. The process as claimed in claim 8, wherein the water content of the solvent is approximately 0.5%.

12. The process as claimed in claim 1, wherein the solvent is methanol, ethanol, or 2-propanol.

13. The process as claimed in claim 1, wherein the 3R,2'R stereoisomer of glycopyrronium bromide or iodide (formula II: A=Br or I),

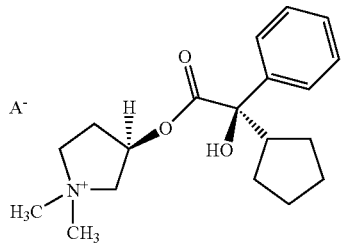

II is isolated.

14. The process as claimed in claim 1, wherein the 3S,2'S stereoisomer (formula IV: A=Br or I),

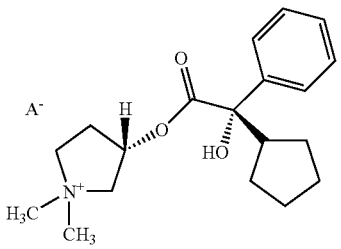

IV is isolated.

15. The process as claimed in claim 1, wherein the 3R,2'S stereoisomer of the thienyl analog of glycopyrronium (formula VI: A=Br or I),

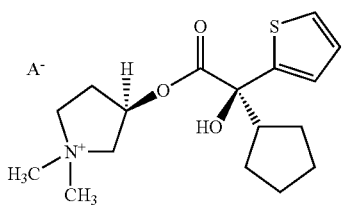

VI is isolated.

16. The process as claimed in claim 1, wherein the 3S,2'R stereoisomer (formula VIII: A=Br or I),

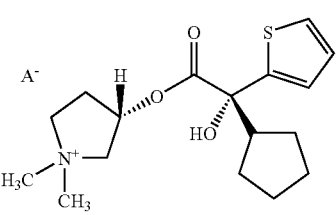

VIII is isolated.

* * * * *